(12) United States Patent
Roslyakov et al.

(10) Patent No.: US 10,335,349 B2
(45) Date of Patent: Jul. 2, 2019

(54) PRESCRIPTION DRUG ABUSE PREVENTION SYSTEM

(71) Applicant: Addinex Technologies, Inc., New York, NY (US)

(72) Inventors: Stanislav Roslyakov, New York, NY (US); Jay Howard Schiff, New York, NY (US)

(73) Assignee: Addinex Technologies, Inc., New York, NY (US)

( * ) Notice: Subject to any disclaimer, the term of this patent is extended or adjusted under 35 U.S.C. 154(b) by 0 days.

(21) Appl. No.: 16/012,081

(22) Filed: Jun. 19, 2018

(65) Prior Publication Data

US 2018/0360693 A1    Dec. 20, 2018

Related U.S. Application Data

(60) Provisional application No. 62/522,358, filed on Jun. 20, 2017.

(51) Int. Cl.
| | |
|---|---|
| *B65D 83/04* | (2006.01) |
| *A61J 7/00* | (2006.01) |
| *A61J 7/04* | (2006.01) |
| *G16H 20/13* | (2018.01) |
| *A61J 7/02* | (2006.01) |

(52) U.S. Cl.
CPC .......... *A61J 7/0076* (2013.01); *A61J 7/0427* (2015.05); *G16H 20/13* (2018.01); *A61J 7/02* (2013.01); *A61J 2200/30* (2013.01)

(58) Field of Classification Search
CPC .......... A61J 7/0076; A61J 7/0427; A61J 7/02; A61J 2200/30; G16H 20/13

USPC ............ 206/459.1, 528, 533, 536, 538, 539; 116/308, 309, 317, 318; 221/25, 87

See application file for complete search history.

(56) References Cited

U.S. PATENT DOCUMENTS

| | | | |
|---|---|---|---|
| 3,421,347 A | | 1/1969 | Sotory |
| 5,358,117 A | * | 10/1994 | Adams ...................... A61J 7/04 |
| | | | 116/308 |

(Continued)

FOREIGN PATENT DOCUMENTS

WO    2017139761 A1    8/2017

OTHER PUBLICATIONS

International Search Report, US Patent and Trademark Office, Application No. PCT/US2018/038282, dated Sep. 7, 2018.

(Continued)

*Primary Examiner* — Luan K Bui
(74) *Attorney, Agent, or Firm* — Gottlieb, Rackman & Reisman, P.C.

(57) ABSTRACT

A container storing pills or other discrete objects and which provides restricted access to the pills. The container has a rotatable pill drum allowing selective access to pills when the drum is rotated to various dispensing positions. A rotatable combination disk or other component is provided that has a plurality of channels formed therein and which can be rotationally locked to the drum. Movable pegs engage the channels. Each dispensing position has an associated peg position combination. Rotation of the pill drum from one dispensing position to the next is blocked unless the pegs are moved into the appropriate peg position combination. The pill drum can be rotated from one dispensing position to the next using a handle or via an automatic spring loaded mechanism.

20 Claims, 18 Drawing Sheets

(56) References Cited

U.S. PATENT DOCUMENTS

| | | | |
|---|---|---|---|
| 5,562,231 A * | 10/1996 | Lambelet, Jr. | B65D 83/0454 206/531 |
| 5,597,072 A | 1/1997 | Lieberman et al. | |
| 6,003,467 A * | 12/1999 | Shelton-Ferrell | G09F 11/23 116/308 |
| 6,364,155 B1 * | 4/2002 | Wolfe | B65D 83/0454 221/121 |
| 7,996,106 B2 | 8/2011 | Ervin | |
| 8,020,415 B2 | 9/2011 | Corbin et al. | |
| 8,483,872 B2 | 7/2013 | Ratnakar | |
| 8,666,539 B2 | 3/2014 | Ervin | |
| 8,967,378 B2 * | 3/2015 | Schapiro | A61Q 11/00 206/369 |
| 9,014,847 B2 | 4/2015 | Dunn | |
| 9,235,689 B2 | 1/2016 | Ervin | |
| 9,542,534 B1 | 1/2017 | Ducatt et al. | |
| 9,665,691 B2 | 5/2017 | Ervin | |
| 9,731,103 B1 | 8/2017 | Rouse et al. | |
| 9,731,853 B2 | 8/2017 | Akdogan et al. | |
| 9,824,191 B2 | 11/2017 | Ervin | |
| 9,836,583 B2 | 12/2017 | Garcia et al. | |
| 9,870,450 B2 | 1/2018 | Blackburn | |
| 2002/0030062 A1 * | 3/2002 | Garrant | B65D 83/0409 221/87 |
| 2008/0179387 A1 | 7/2008 | Cantlay et al. | |
| 2011/0049079 A1 | 3/2011 | Simpson | |
| 2011/0079058 A1 | 4/2011 | Nielsen et al. | |
| 2013/0075418 A1 | 3/2013 | Sack et al. | |
| 2013/0110283 A1 | 5/2013 | Baarman et al. | |
| 2015/0217930 A1 | 8/2015 | Holmes et al. | |
| 2016/0107820 A1 | 4/2016 | Macvittie et al. | |
| 2017/0083686 A1 | 3/2017 | Hawkins et al. | |

OTHER PUBLICATIONS

Written Opinion of the International Searching Authority, US Patent and Trademark Office, Application No. PCT/US2018/038282, dated Sep. 7, 2018.

Dr. Clive Stack, Dr. Gwenyth James, Proposal for Remote Dosing Program, http://www.humanitas.org.au, pp. 1-49, Stack & James 2010.

Sushil G. Patil, Timothy J. Gale, Preliminary Design of Remotely Used and Monitored Medication Dispenser, https://humanitas.org.au/wp-content/uploads/Preliminary-Design-of-Remotely-Used-and-Monitored-Medication.pdf, Proceedings of the 28th IEEE EMBS Annual International Conference, New York City, USA, Aug. 30-Sep. 3, 2006, pp. 3616-3619, School of Engineering, The University of Tasmania, Hobart, Tasmania, Australia.

* cited by examiner

PRESCRIPTION DRUG ABUSE PREVENTION SYSTEM

CROSS-REFERENCE TO RELATED APPLICATIONS

This applications claims priority to U.S. Patent Application Ser. No. 62/522,358, filed Jun. 20, 2017, the entire contents of which is expressly incorporated by reference.

FIELD OF THE INVENTION

This present invention relates to an apparatus for storing pills or other discrete objects and which provides restricted access to the pills. More specifically, the invention concerns various containers that can be used to dispense pills individually and which have a mechanical locking assembly that permits access to pills only on entry of consecutive passwords.

BACKGROUND

Physicians and pharmacists frequently prescribe medications that must be taken in limited quantities. When the medicine is dispensed in a conventional pill bottle, it is up to the patient to self-regulate the number of pills that they take at any one time. While a doctor may refuse to refill a prescription before a certain period of days has elapsed, such as 25 days into a 30 day prescription, the patient may still take too many pills during that time.

Restricted access to pill containers can be provided by including a combination or other lock on the cover. Without the combination, the container cannot be opened. However, once a patient has the combination and opens the container, they can access the all of the pills inside.

Various attempts have been made to provide a pill container that dispenses one or a limited number of pills upon entry of a password. Existing devices rely on electrical mechanical system that can be complex to manufacture. In addition, by relying on electrical components, the device may fail to operate if the battery is dead, possibly depriving the patient of critical medication. Further, these devices can be difficult to recycle particularly because of the difficulty and expense required to sterilize electrical parts without damaging them. As a result, such containers can be costly to provide for use.

Accordingly, there is a need to provide a locking container that allows limited access to stored pills upon entry of a password and which does not rely on electronic or electronical mechanical apparatus.

There is a further need to provide such a locking container that, allows sequential access to stored pills upon entry of sequential passwords and which can be easily configured with a wide variety of passwords with minimal changes to the system assembly.

Yet a further need is to provide such a locking container that can be easily filled with medication during manufacturing or by a doctor or pharmacist dispensing the medicine and which cannot easily be opened by a patient who lacks the proper combinations.

An additional need is to provide a locking container that can be easily be recycled and where most or all of the parts can be sterilized for reuse.

SUMMARY

These and other problems are solved by a dispensing device that has a housing with a pill storage drum inside that can be rotated to a number of dispensing positions. Each dispensing position allows user access to a pill storage area of the drum through an opening in the housing. A combination disk, cylinder, or surface rotationally locked with the drum is provided with a plurality of channels formed therein. Movable pegs mounted to the housing engage the channels. The channels are configured so that movement of the drum from one dispensing position to the next requires moving the pegs to a specific combination position. To access a further dispensing position, the pegs must be set to a different combination position.

In one configuration, pegs have a plurality of predefined shapes, such as varying length and widths. The channels comprise a set of rest channels. The pegs are positioned in the rest channels with the drum is at a dispensing position. The rest channels have a shape which will allow every peg shape to slide within it. A plurality of transition channels are provided to connect adjacent rest channels. The transition channels are shaped to allow some or only one of the peg shapes to pass while blocking other shapes. To advance the drum from one dispensing position to the next, each peg must be positioned so that it is adjacent an appropriately shaped transition channel. The peg arrangements permitting movement from one dispensing position to the next can be indicated by combinations of letters, numbers or other indicia formed on the housing.

In one configuration, the drum is rotated manually using a handle on a rotatable shaft that engages the drum and/or combination disk. In another configuration, the device is spring loaded and entry of the proper peg combination will allow the spring to automatically advance the drum to the next dispensing position.

The peg combinations needed to access to the medicine in a given container can be changed during manufacturing by using combination disks or cylinders with different channel configurations and by changing the specific peg shapes selected for use in any given assembly. The particular combination disk structure and the shape and positioning of pegs used in a given container can be recorded during manufacturing and used to determine the set of combinations for that container. This information can be linked to a unique container ID so that the combinations for a particular container can be accessed. When a container is dispensed to a patient, the unique container ID can be linked to a patient profile to allow access to the peg combinations for that container with reference to the patient ID or container ID.

Peg combinations to access the pills stored in a container can be issued to patients in a limited manner using various systems. To limit access to the medicine, a patient may be given only one peg combination at a time. To get a second pill, the patent must request the next peg combination for their container, such as by accessing a central server using, e.g., an Internet APP, or if Internet is not available by calling their doctor, pharmacist, or an automated or manned text-in or call-in service.

In practice, a pharmacist dispensing pills in a container according to the invention can use a prepackaged device or load an empty device with the prescribed medication. A manufacturer can provided prescription pills in a preformed pill drum which can be inserted into the container before the container is closed. The container can be provided in a partially assembled or unlocked configuration that allows pills to be placed into the container manually by rotating the pill drum to each dispensing position and putting the pill into the associated chamber in the housing. After the pills are added, the container is fully closed, upon which the pill drum is prevented from rotating without entry of the proper combinations.

When the patient is done with the container, it can be returned to a manufacturer, such as by the patient using a prepaid mailer received with the container. On receipt of a used container, any remaining medicine can be removed and accounted for. The container can be checked for damage and misuse various components can be sterilized for reuse. Usage reports and other information can be generated for use by doctors, insurance companies, EMR or state wide prescription drug monitoring program (PDMP) systems, among others.

The system solves several problems and can be particularly useful in helping to address improper use of prescription opioids and other addictive or expensive drugs (e.g. amphetamines or ADD medication). The system helps prevents overdoses by preventing at-home dispensing in excess of doctor's prescription so patient cannot take more at a time than prescribed. A pill combination password dispensing system can lockout a patient from receiving additional passwords to access the pills, even if a container is not empty, if the prescription expires or other relevant conditions are detected. Dosages can be monitored by tracking how often a patient requests new passwords. Drug security is increased by restricting access to children and other individuals who do not have the passwords. The restricted access container may also reduce crime by making it more difficult to access the prescribed pills without breaking the container, which may also damage or destroy the internal medicine.

BRIEF DESCRIPTION OF THE FIGURES

These and other features and advantages of the invention, as well as structure and operation of various implementations of the invention, are disclosed in detail below with references to the accompanying drawings, in which.

DETAILED DESCRIPTION OF VARIOUS EMBODIMENTS

Figure 1A:
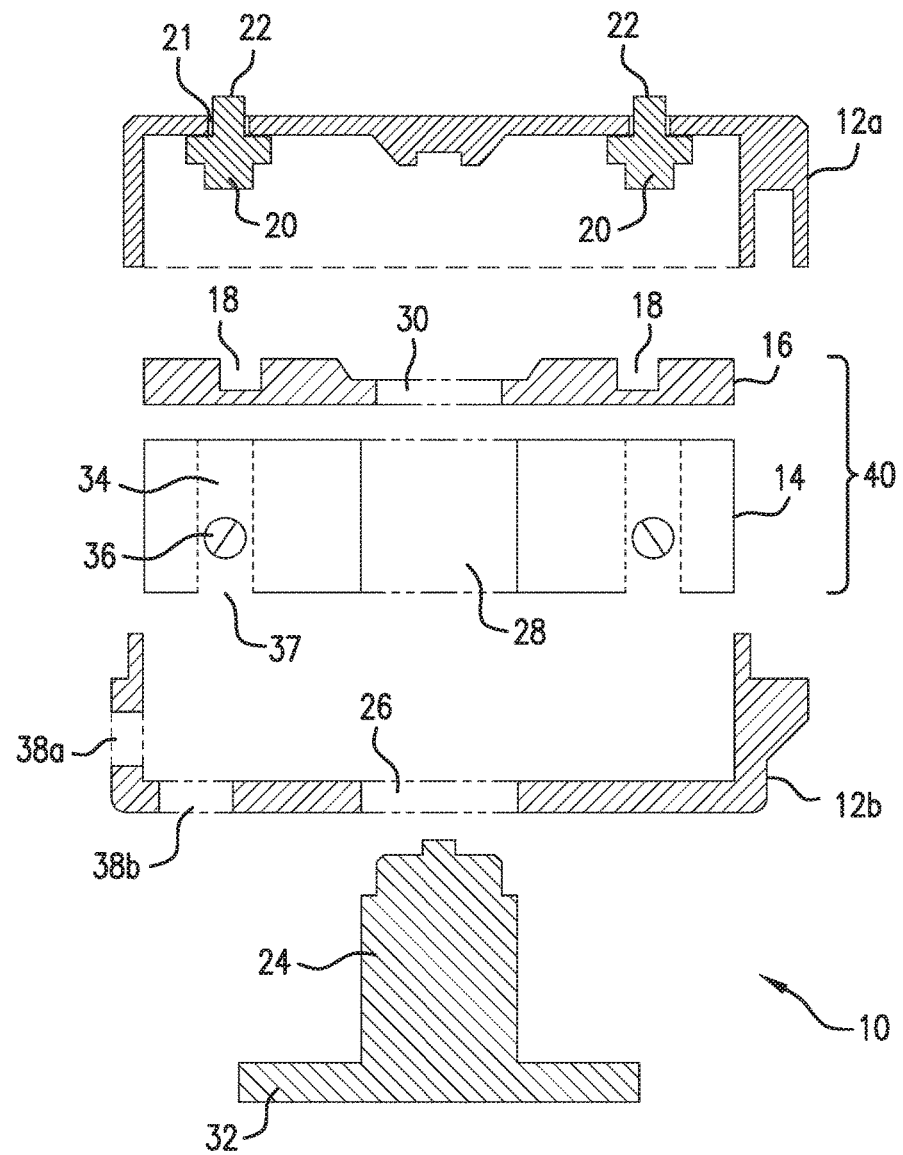
FIG. 1A shows a simplified exploded cross-sectional view of a first embodiment of a container according to aspects of the invention.

One aspect of the present invention is a mechanical container for securely storing and individually dispensing pills or other discrete objects. FIG. 1A is a simplified exploded cross-section of one embodiment of a container 10. The container 10 comprises an outer shell or housing 12 with a top 12a and bottom 12b that can be connected to each other, preferably via a permanent attachment. The interior of the housing 12 is generally cylindrical and contains a pill drum 14 and a combination disk 16, both of which can be rotated within the housing 12 along a central axis. The shell, drum, and combination disk can be made of various rigid materials, such as metal or plastic.

An axial shaft 24 extends through an opening 26 in the bottom of the housing 12 and engages the pill drum 14 and disk 16 within central holes or openings 28 and 30, respectively. The components are configured so that the drum 14, and disk 16 each engage the shaft, such as through mating parts such as slots and grooves, and are rotationally locked to the shaft and thereby also rotationally locked to each other to form a rotatable drum assembly 40. Rotating the shaft 24, such as by use of a handle portion 32, allows user to rotate the drum assembly 40.

The pill drum 14 has a number of Internal chambers 34 into which pills 36 or other objects can be placed. A pill can be accessed by a user when the pill drum 14 is rotated to a dispensing position where an opening 37 to a chamber 34 is aligned with an access opening in the housing 12, such as an opening or port 38a, 38b. To access the next pill, the drum assembly 40 is rotated to the next dispensing position where the opening 37 of the next chamber 34 is in position relative to access opening in the housing. The drum assembly 40 can be rotated from a start dispensing position which permits access to the first chamber to an end dispensing position which permits access to the last chamber. Alternatively, the pill drum can contain pills in preformed blister pack.

As will be discussed in more detail below, the disk 16 has an arrangement of channels 18 formed on its surface. One or more movable pegs 20 are configured to engage the channels 18 in the disk 16. The pegs 20 are movable in at least a horizontal or vertical direction between two or more positions. Top portions 22 of the pegs 20 extend through respective slots 21 in the housing 12 and can be used to change the position of the pegs.

The channels 18 are configured so that there is a traversal path 54 that can be followed by each peg 20 as the disk is rotated from the start dispensing position to the end dispensing position and which path requires the position of that particular peg to be changed at least once.

Each peg can have a unique traversal path 54 through which it can pass as the drum 14 and thus disk 16 is rotated from a start dispensing position to the end dispensing position. Preferably, the channels 18 are configured so that with the pegs 20 in a first position, the drum assembly 40 can only be rotated to the next dispensing position before at least one of the pegs 20 is blocked and thereby prevents further rotation. The channels 18 are further configured so that the disk 16 can be rotated to the next dispensing position only after one or more of the pegs 20 are moved into a different position. A ratchet mechanism can be provided to allow the drum assembly 40 to be rotated in one direction.

Thus, for example, if there are sixteen pill chambers 24 arranged around the periphery of the pill drum 14, the channels can be configured so that the drum assembly 40 can only be rotated 1/16 of full turn for a given position of the pegs. To rotate the drum assembly 40 an additional 1/16 of a turn to the next dispensing position where the next pill chamber can be accessed, the user must move at least one of the pegs to a different position. It should be appreciated, though, that movement from the start dispensing position to the end dispensing position may not require rotation of the drum through a full 360 degrees.

Each predefined peg position can be defined by letters, numbers, colors, brail indicators, or other indicia indicators on the housing. A dial, slider, or other component can be connected to peg to point to a specific indicator and corresponding the peg's current position. The numbers or other indicia can be used to reference the peg position combinations which are needed to allow the drum assembly 40 be advanced from a given dispensing position to the next dispensing position.

To produce containers 10 with different sets of rotation combinations, different channel configurations can be provided, e.g., by using differently configured combination disks in the container. A selection of combination disks 16 can be predefined and made available during assembly of the container. Although combination disks 16 are shown with channels on only one surface, disks 16 can be provided with different channel configurations formed on the opposite side.

Preferably, a new peg configuration is required to rotate the drum from one dispensing position to the next. However, the channels can be further configured so that the drum assembly 40 can be moved to two or more dispensing positions for a single peg configuration. This may be useful, for example, in allowing access to more pills than can fit in a single chamber without requiring multiple containers. Also, while the pill chambers 34, and thus the corresponding dispensing positions can be symmetric and equally spaced within the pill drum 14, the rotational distance between consecutive dispensing positions and the size of the pill chambers can vary.

Restricted access to the pills in the container 10 can be managed by providing, a user with the pill combination needed to advance the drum assembly to the next position on a restricted basis or periodic basis, such as once a day or no more than three times a week.

In the embodiment of FIG. 1A, the drum 14, disk 16, and shaft 24 are separate components and both the drum 14 and disk 16 mechanically engage the shaft 24 when it is inserted. Preferably, when the shaft 24 is partially inserted it engages the 14 drum and allows rotation of the drum 14 independently of the disk 16 to allow loading of the drum with pills without requiring entry of combinations. When the shaft 24 is fully inserted, it engages the drum 14 and the disk 16, rotationally locking them together.

Figure 1B:
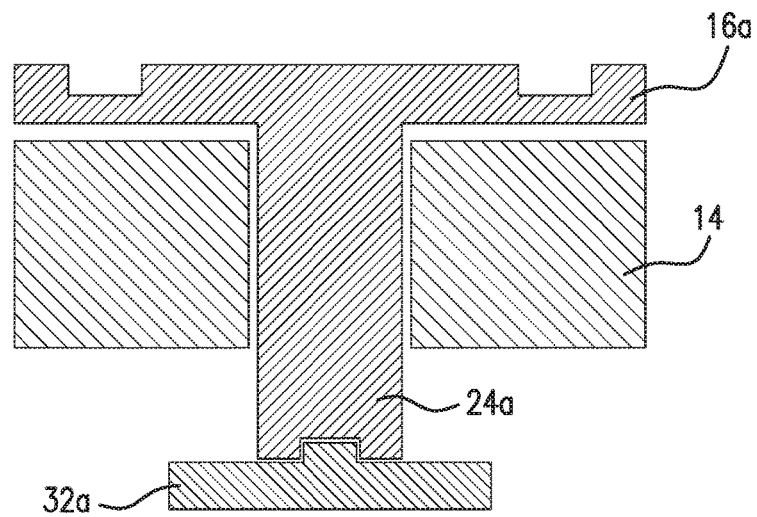
FIGS. 1B-1D show alternative configurations for connecting internal parts of the container of FIG. 1.
Figure 1C:
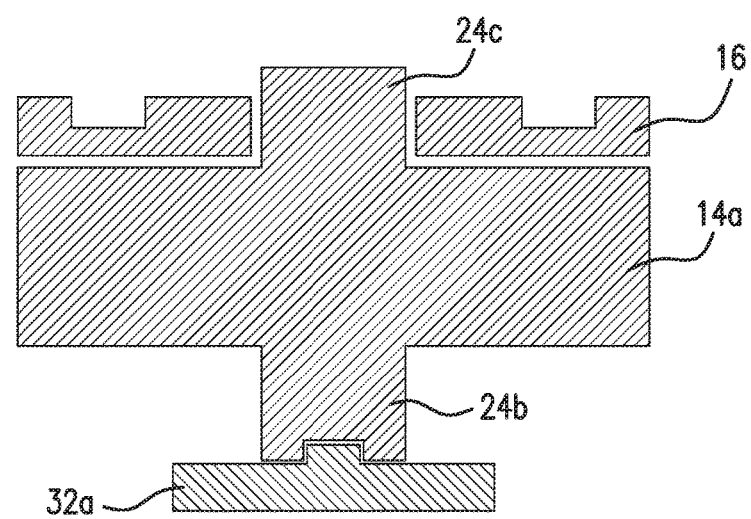
Figure 1D:
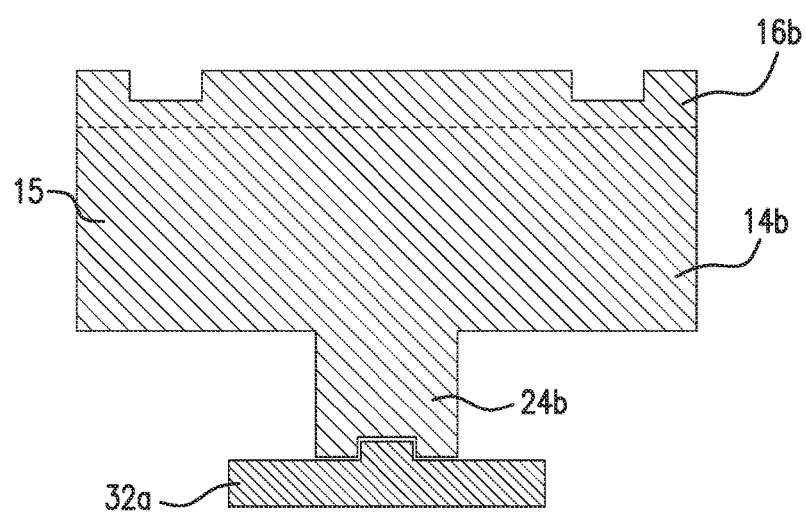

Alternatively, one or more of the drum, disk, and shaft elements can be permanently attached to each other, such as by glue or ultrasonic welding. In alternative configurations, one or more of these components can be combined into an integrally formed part. FIG. 1B shows a combination disk 16a with an integral shaft 24a. (Housing 12 and pegs 20 have been omitted for clarity.) The pill drum 14 engages the shaft 24a. A handle 32a can be connected to the end of the shaft 24a FIG. 1C shows a pill drum 14a having an integral lower shaft 24b and upper shaft 24c. The disk 16 engages the shaft 24c. A handle 32a can be connected to the end of the shaft 24b. In FIG. 1D, a combined pill drum and combination disk 15 is shown having lower pill drum portion 14b and upper combination disk portion 16b. An integrally formed shaft 24b and attachable handle 32a are also shown, similar to FIG. 1C.

Figure 2:
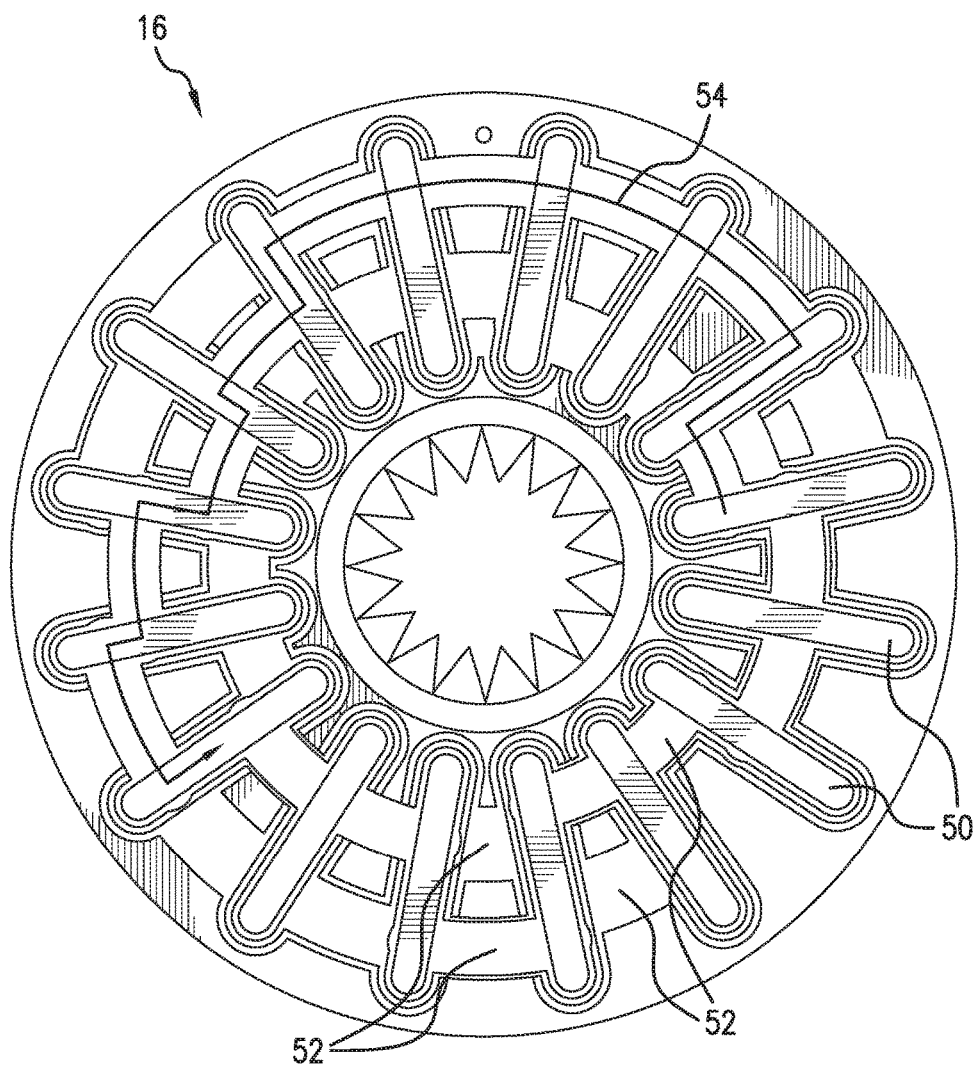
FIG. 2 is a plan view of an embodiment of a combination disk.

With reference to FIG. 2, the plurality of channels 18 in disk 16 preferably comprise a plurality of rest channels 50 with one or more transition channels 52 connecting each pair of adjacent rest channels. A rest channel 50 is a channel in which a peg can slide freely between its predefined positions when the disk 16 is at a dispensing location. A transition channel 52 provides a path for a peg to take as the disk is rotated to the next dispensing location. To travel a transition channel 52, a peg must be in the correct predefined location.

In the example disk 16 of FIG. 2, the transition channels are located at one of 4 different radial positions and to follow the traversal path as the disk 16 is rotated, the peg must be repositioned when at certain dispensing positions to allow the disk to rotate and advance the drum to the next dispensing position. An example traversal path 54 for a given peg is shown in FIG. 2.

The pegs 20 can have a plurality of different predefined physical shapes. The rest channels 50 are configured with a 'universal' cross section that can accommodate a peg having any of the predefined shapes. Each transition channel 52 is configured to accommodate a peg having one or more of the predefined shapes while blocking passage of at least one other of the predefined shapes. Preferably, the transition channels are configured so that only one of the predefined peg shapes can pass through.

Figure 3:
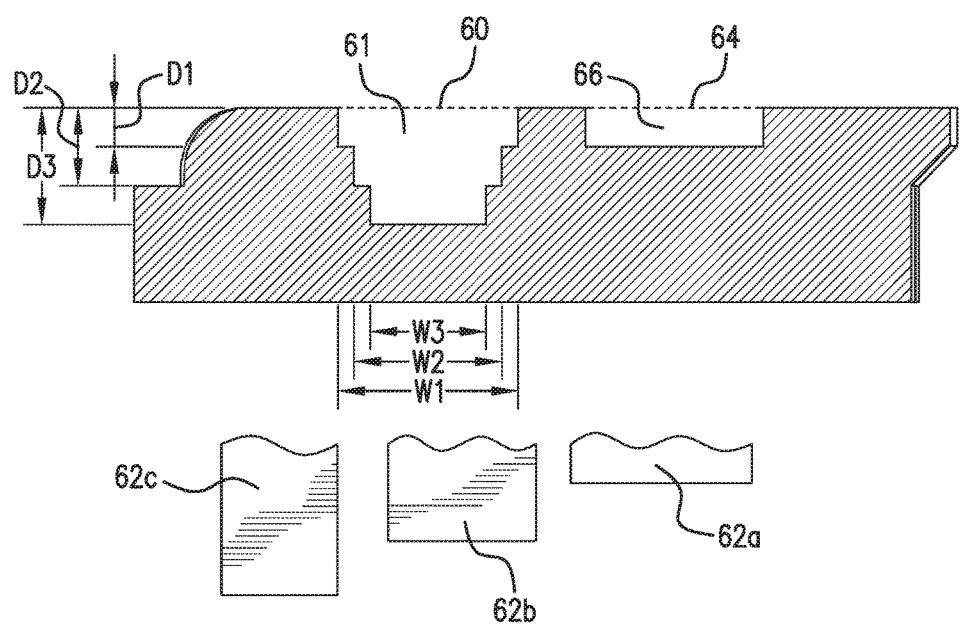
FIG. 3 shows a partial cross section of an example combination disk and various peg shapes.

In one embodiment, the channels 18 have a cross-section with predefined widths and depths. FIG. 3 shows a channel 60 with channel walls defining a universal cross section area 61 having, in this example, a stepped-cross section with decreasing widths and corresponding increasing depths, such as widths W1, W2, W3 and corresponding depths D1, D2, and D3. This channel can accommodate any peg with a shape that fits into cross section area 61, for example, pegs 62a, 62b, and 62c having predefined width and lengths W1/D1, W2/D2, and W3/D3, respectively.

Transition channels define a transition cross section which comprises only a portion of the universal cross section 61 section and which can accommodate fewer than all of the predefined peg shapes. For example, channel 64 of FIG. 3 defines a cross-section 66 which includes only a portion of the universal cross-section FIG. 3. Channel 64 may have width and depth D1 and so will pass peg 62a but block pegs 62b and 62c which both need a deeper channel. Likewise, a channel with a top-to-bottom width W3 and depth D3 will define a cross-section that will only pass peg 62b. There should be the same number of transition channels 52 between adjacent rest channels 50 as the number of different predefined peg shapes being used in a given container and the shape of each peg must match at least one of the transition channel cross-sections to allow traversal there through.

Figure 4:
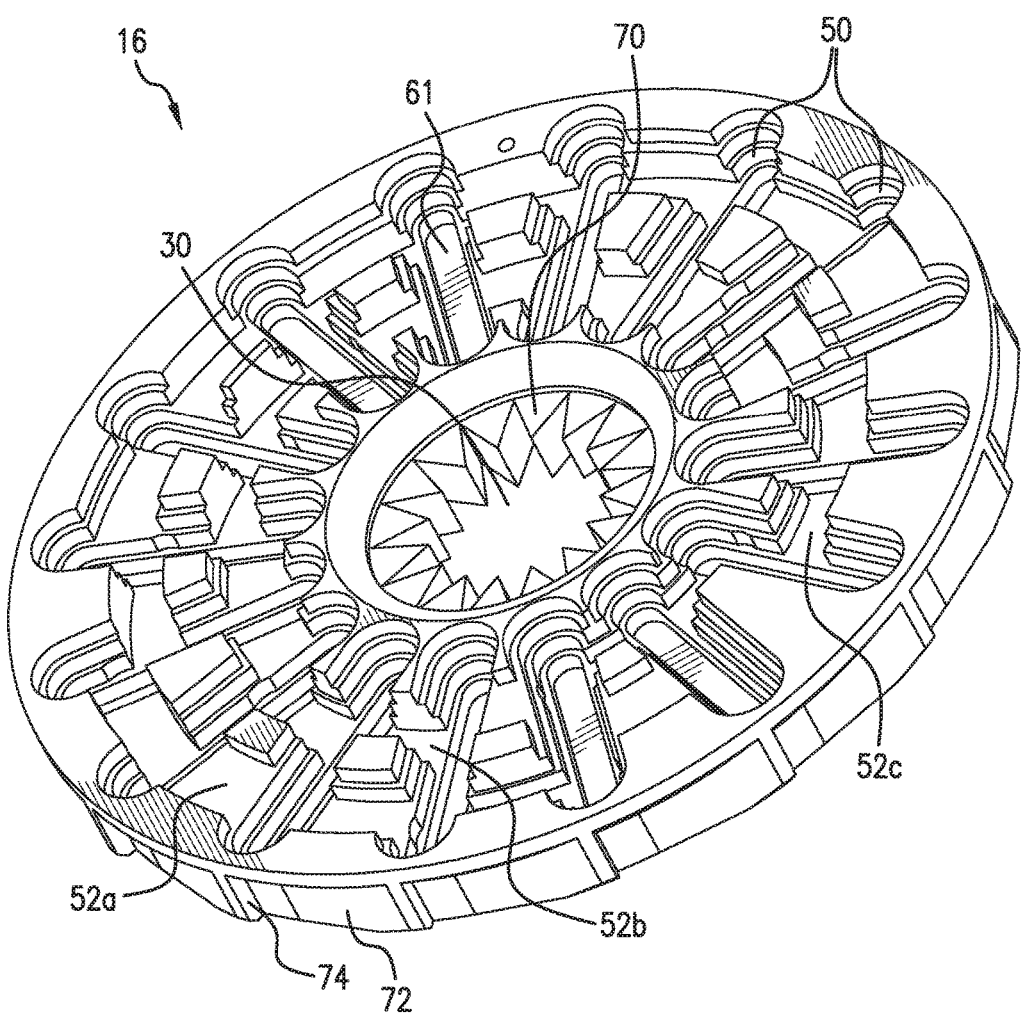
FIG. 4 is a perspective view of an embodiment of a combination disk; is

FIG. 4 shows a perspective view of an exemplary combination disk 16 with rest channels 50 that each have a universal cross-section 61. One or more transition channels are formed between adjacent rest channels, such as transition channels 52a, 52b, and 52c defining different cross-sections which will allow one or more peg shapes to pass while blocking other shapes.

Thus, in this configuration, different transition channels can have different depth levels in which pegs of different sizes must slide. The shorter pegs are wider which limits their depth to transition channels of the highest levels on the combination disks or cylinder, while the longer pegs are narrower which allows them to reach down to the lowest level on the combination disks. Therefore, every peg has a unique transition channel through which it can pass. A narrow peg that protrudes deeper into the disk could pass through a narrow deep transition channel while a wide short peg, could not and vice versa. The arrangement of peg shapes provided with dispensing devices can be varied so different containers have different shaped pegs with varying depth and diameter.

Also shown in FIG. 4 is a hole or opening 30 to receive the shaft 24 and teeth 70 which engage corresponding grooves in the shaft. The disk 16 may also be formed with angled detents or gear teeth 72 with surfaces 74 that can engage a pawl of a ratchet assembly connected to the housing. Preferably, there is one detent tooth 72 associated with each transition channel.

The possible location of transaction channels per depth level that can exist after manufacturing of each unique disk or cylinder corresponds directly to all the possible locations a peg can be moved for each password entry. Such locations are aligned with a slider, dial, or other part connected to the top portions 22 of the pegs and which points to the "numerical indicators" or other indicia on the outer-shell. If a pin configuration 'password' is entered correctly by a user, the pegs can successfully slide to the next rest channels, allowing the drum to rotate. After rotation each peg ends up in the next resting channel.

To make it more difficult for a patient who has the combination set for one device to figure out combinations for another, the indicia need not correspond, to the particular peg size or shape, but rather provide only an indication which allows a peg to be positioned in its predefined positions. For example, a Red dial or slider or a slider designated A may always be in the same peg guide slot in the housing relative to the device for different instances of the device, but the configuration and peg size attached below the surface can be different. This will make it more difficult to use an algorithmic method to deduce passwords across different devices since the configuration will be different among devices.

As noted, pills can be accessed through opening or port 38. The port 38 can also contain a sealing hatch, preferably providing a water-proof or water resistant closure. The hatch can prevent preventing pills from falling out after drum rotation to a dispensing position and also help reduce drug degradation due to elements in the exterior environment. If the drum that is used contains medication stored in a blister pack variety or equivalent, a pill pusher can also be provided that passes through a secondary port 38b in the housing and can be used to press the pill out of the blister pack through a through the main opening 38a. In one configuration, the hatch can deadbolt the drum from rotation and be configured so that the drum cannot spin when the hatch is open. This will prevent users from trying to stick objects into the medication dispense opening attempting to rotate the drum without entry of the combination. The hatch can also be inversely linked to the drum and peg setting dials, so as to require the hatch to be opened for the drum to spin but so as to lock the dials in place when open. This would make guessing the password much more onerous and time consuming, since the patient would have to open and close the hatch after every try.

Referring to FIGS. 5A-5G, there is shown an exploded view of a particular embodiment of a container 100 and various components therein. As with the embodiment of FIG. 1, this container uses a manual handle to provide the turning force to rotate the internal components. The container has a housing 112 with upper and lower parts 112a and 112b, pill drum 114, and combination disk 116. Shaft 124 passes through hole 126 in the bottom of the housing 112.a and through opening 128 and 130 in the drum 114 and disk 116 respectively. The shaft has engaging surfaces that mate with corresponding surfaces on the drum and disk. For example, tongues 129 within the opening 128 of the drum 114 engage corresponding grooves 133 on the shaft 124 to rotationally lock the drum 114 to the shaft. Teeth 125 on the shaft 124 engage corresponding teeth 131 within opening 130 to rotationally lock the disk 116 to the shaft 124.

Access port 138a and port 138b (not shown) can provide access to a pill or other item stored on or in the drum 114 when the drum is at the appropriate dispensing positions.

The pegs 120 can side radially within slots 160 formed on the top of the housing 112a. A sliding tab 162 can be connected to the top portions 122 of the peg extending out of the housing. The tab 162 can be used to adjust the position of the peg 120 within the channels in the disk 116 to one of the predefined peg positions. The tab can also point to indicia 164 adjacent tab 162 to all a user to move the tab to a specified one of its predefined positions. Detents 166 and notches 168 can be used to allow the pegs to snap into position. An internal cover 170 can be provided to hold the peg components in place and radial slots 172 provided in the internal cover 170 through which the pegs extend.

In one embodiment, the peg 120 is centered relative to its top portion 122. In an alternative embodiment, shown in FIGS. 5F and 5G, the peg can be offset from a central axis and the position of the top portions 122 and the system configured so that the peg can be placed in either orientation when inserted into the channels. By changing the orientation of one more pegs, the peg combinations needed to rotate the drum assembly can be easily changed without changing the layout of the channels. A similar effect can be provided by using an asymmetric tab 162 which can be attached in two different orientations and which point to different indicia in each orientation with the peg in the same place. Reversing the tab alters the number or other indicia that the tab 162 points to even though the peg is in the same place.

This orientation change method allows a device to have the same combination disk and orientation at the start, but generate additional peg position combination descriptions. Therefore, a dial or tab 162 that is pointing to numerical indicator X can have a peg at predefined location X or X−n or X+n relative to the transition channel below, where n is the offset value of the dial in question. Therefore, a small number of combination disks can generate many different combination path definitions unique to each device by changing the location and orientation of the pegs.

During assembly, the disk is positioned against the pegs. However, the disk can be placed with the first peg in, any of the rest channels (the remainder will follow due to fixed geometry of the guide rails), therefore creating a different starting point on the disk. This offsets any combination list by that difference. This feature along with offset peg geometry allow this device to have a large combination pool, even when a single type of combination disk is used.

While pegs and transition channels are preferably multi-sized, to provide for a more complex combination pattern, a simpler version can use commonly sized pegs and a single channel at each position. In a more complex version, each slider can have more than one, peg, of the same or different size and in spaced apart locations that can vary from slider to slider to provide a more expanded set of potential combinations.

In one embodiment, the device has four dials with five transition channels resulting in more than 600 possible combinations. However, since the dials can have two possible positions, this results in six numerical indicator positions, which results in more than 1,000 combination definitions which the user can attempt. The 15 rest channels of the disks results in over 3,000 possible disk configurations that can be manufactured. Using a single disk with dial flipping technique can generate over 100 unique device combinations which is increased even further by the ability to start the disk at any point along any of the rest channels. The number of combinations and possible unique devices can be expanded by adding more dial guides, adding more dials or increasing the number of transition channels.

Preferably, there is at least one specific peg position combination of the disk that will never allow the disk to rotate. This combination can be used as the default shipping combination for the pegs, so that the user will never receive the device in an unlocked position or a rotated position at the start of their request cycle.

In a more specific configuration of the embodiment shown in FIGS. 5A-G, four (4) types of dials or tabs are used to position pegs with diameters of 0.25, 0.20, 0.15, and 0.10 inches and depth levels of 1/16, 1/8, 3/16 and 1/4 of an inch respectively. The dial size and construction method is not limited to the current circular peg shape, but can be any shape that restricts travel through certain transition channels. For example, bent metal clips that range in width can be used instead of circular pegs. A peg may also consist of multiple shapes that reach a certain depth but are regarded as one "dial peg". For example, two 1/16 inch wide pegs spaced by 1/8 of an inch next to each and can be counted as one dial peg but would pass only through such geometry and not a single 1/16 of an inch transition channel.

Figure 5A:
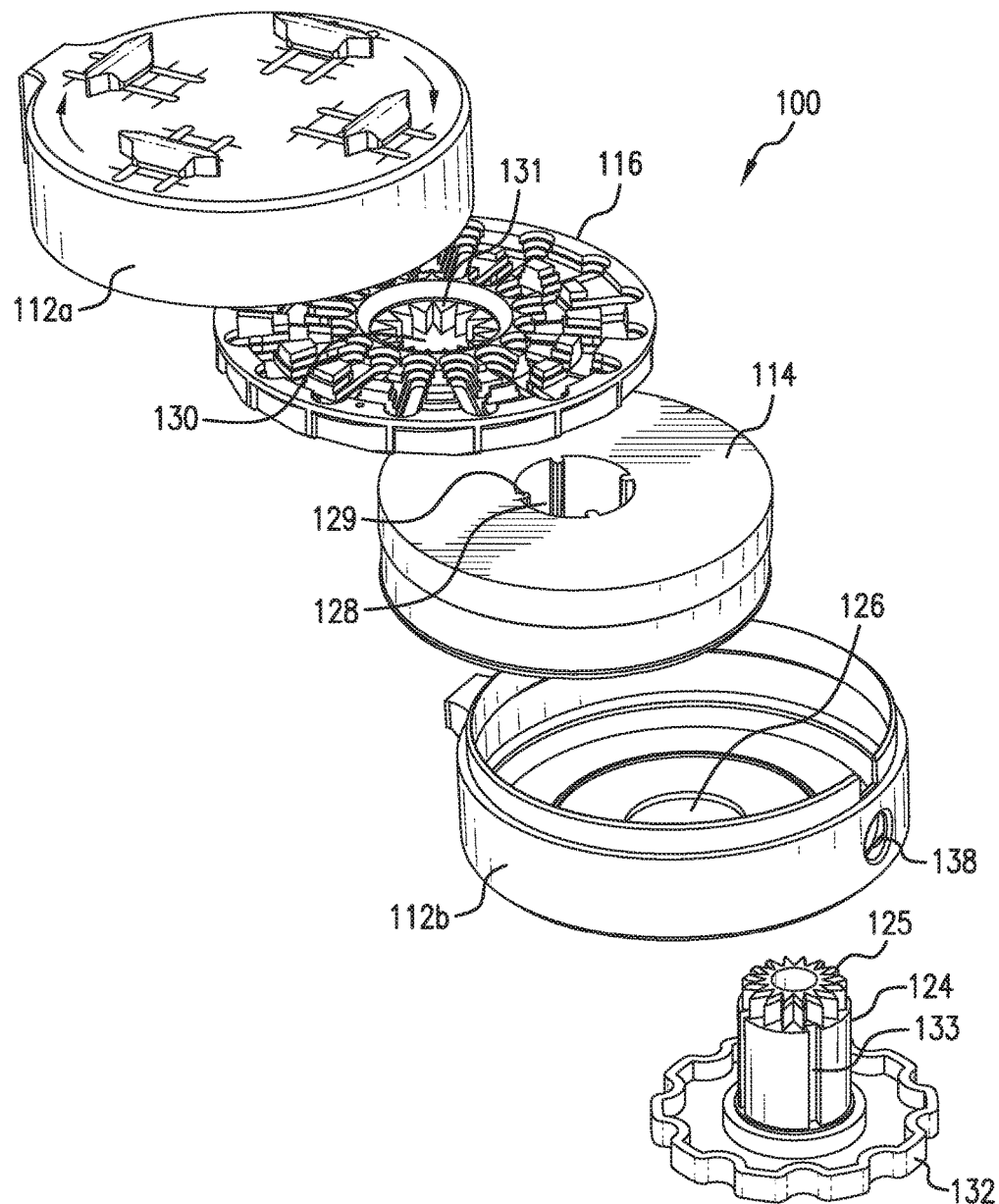
FIGS. 5A-5G show a particular implementation of the first embodiment of a container according to aspects of the invention.
Figure 5B:
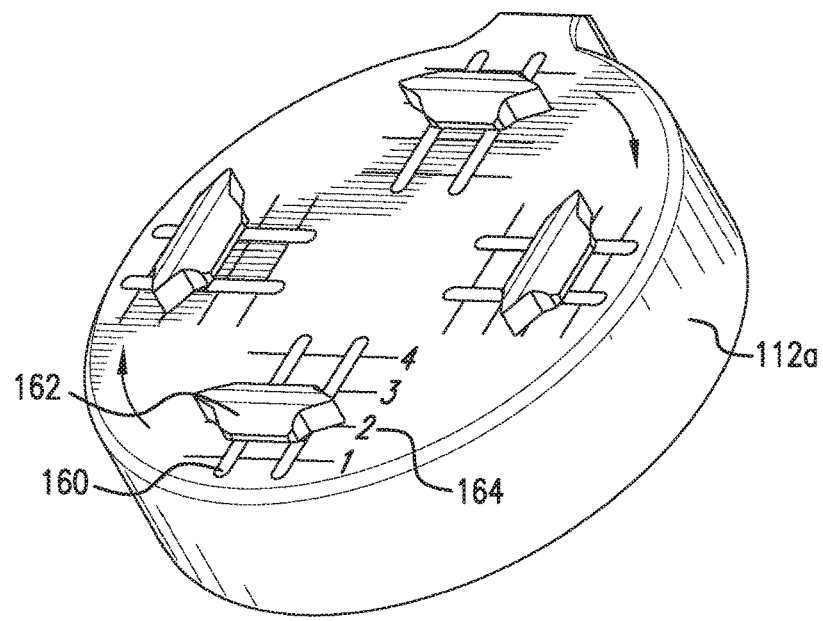
Figure 5C:
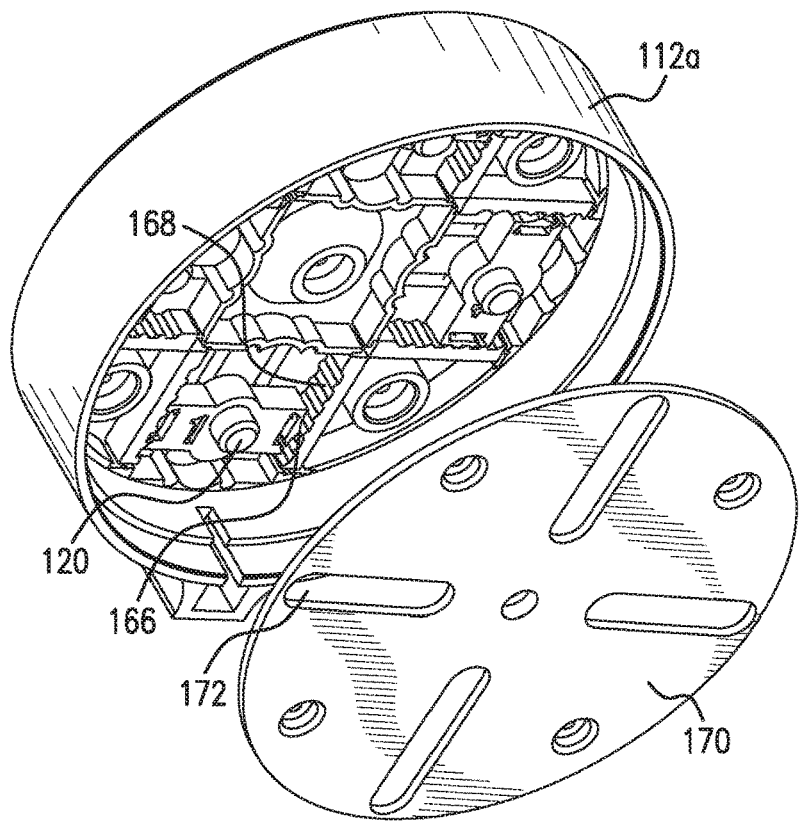
Figure 5D:
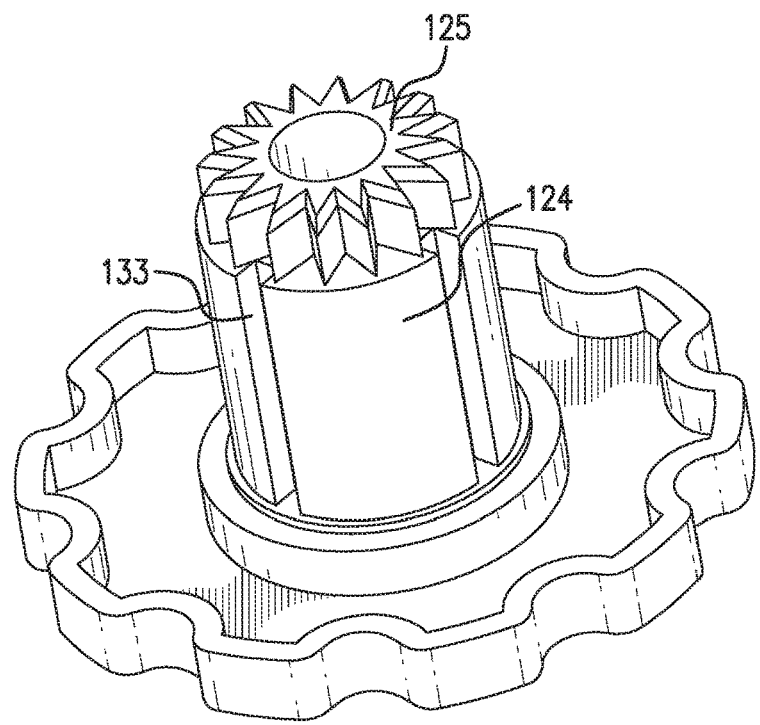
Figure 5E:
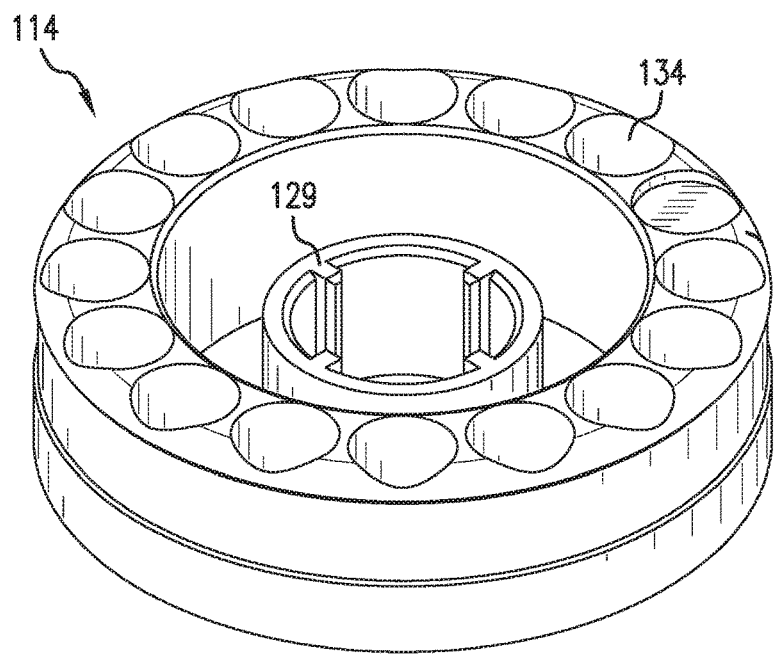
Figure 5F:
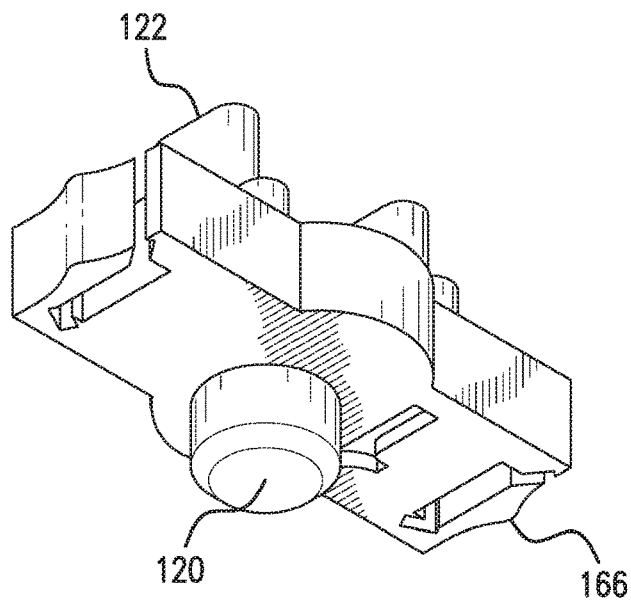
Figure 5G:
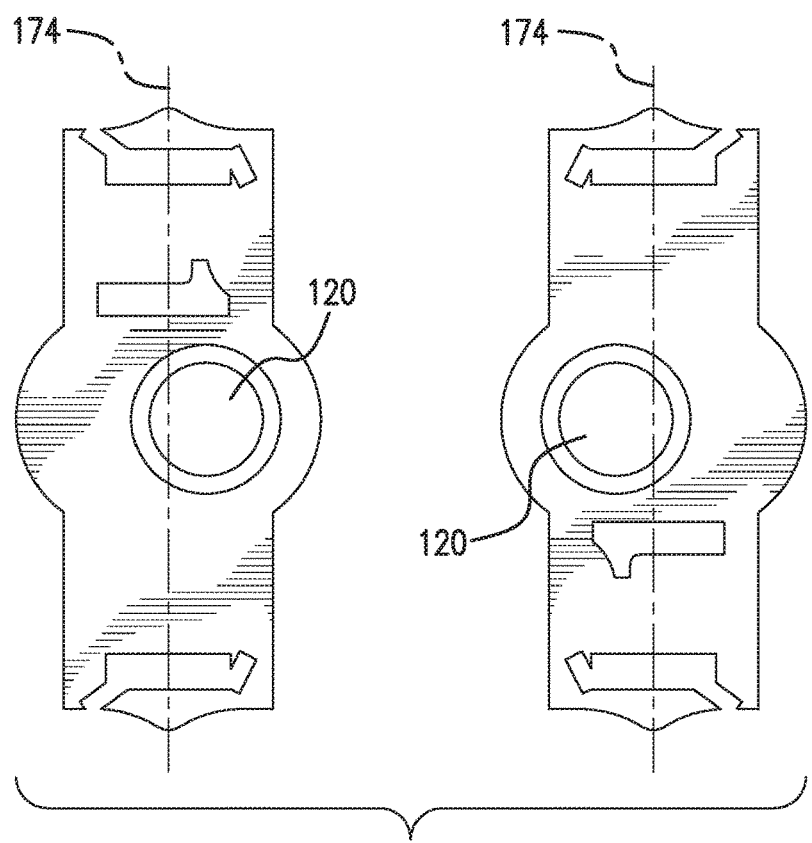

With further reference to FIG. 5D, the shaft 124 with its handle 132 is initially inserted only partially and engages the drum but not the disk. This allows for free rotation of the drum relative to the disk. When the handle is fully pushed in, it locks all three components (drum, disk, shaft) together in a way that only allows rotation if the password combination dials are set to allow the dial pegs to pass, through each transition channel. The device 100 can be shipped to the pharmacy with the handle unlocked to the disk 116 (not pushed in all the way). Advantageously this allows the pill drum to be spun freely by turning the handle. In this configuration, a pharmacist can load the device (drum) with medication in each designated medication storage chambers by inserting all the required doses of medicine in the proper order in the chambers 134.

Once the device is loaded it is turned to the drum's zero location (a position that has no medication and is adjacent the start dispensing point). The handle 132 and shaft 124 is then locked to the disk by a pushing it in the remaining distance. Once the shaft 124 engages the disk 116, it locks the device from further rotation until an appropriate peg combination is entered to allow the drum to turn further. In one configuration, the handle has snap-in hooks or catches to prevent the shaft from falling out of the outer-shell during shipment and before the pill drum is locked. A second set of snap-in hooks or catches can be provided keep the shaft and handle locked to the disk once the handle is fully inserted to lock the container. These hooks limit the handles' ability to move up or down so that the handle can only rotate. Preferably the device is shipped with a spacer between the handle and the shell to prevent accidental locking. This spacer is removed before locking.

Figure 6A:
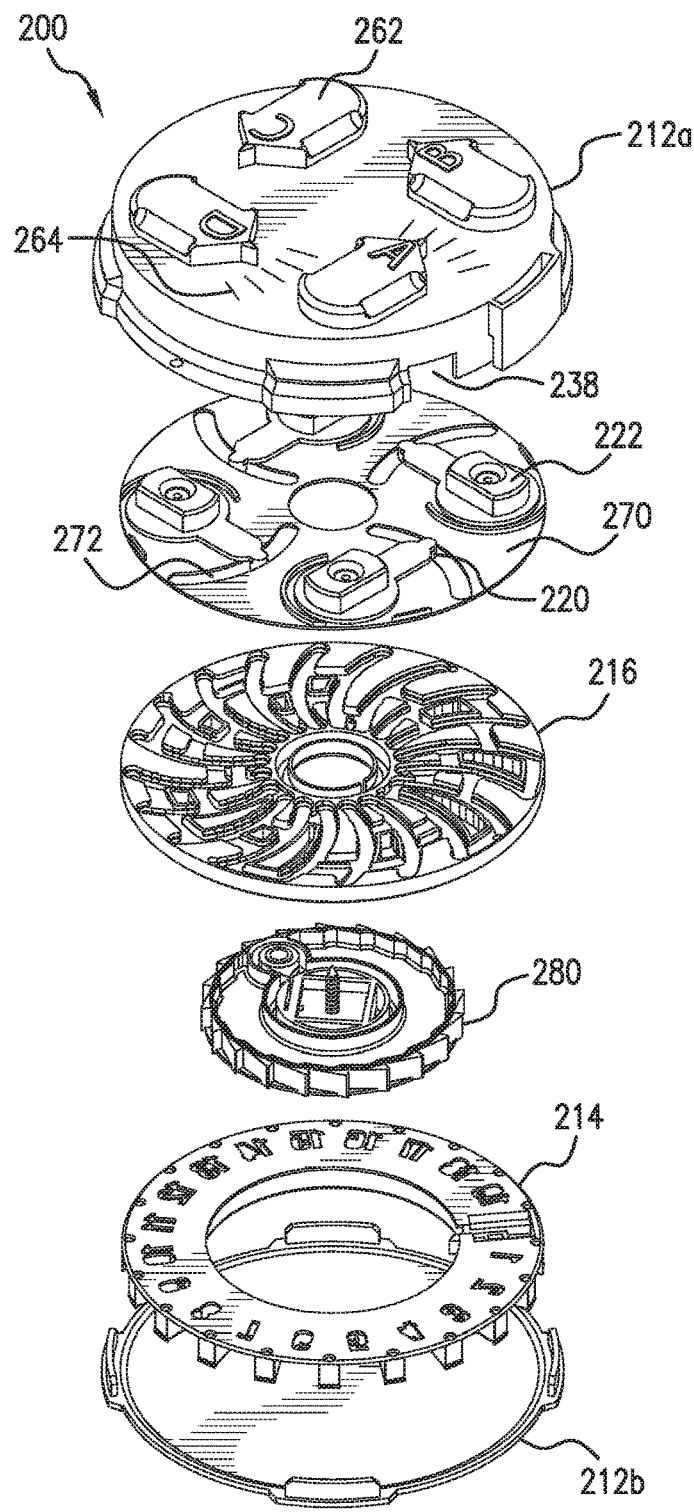
FIGS. 6A-6C show a second embodiment of a container according to aspects of the invention.
Figure 6B:
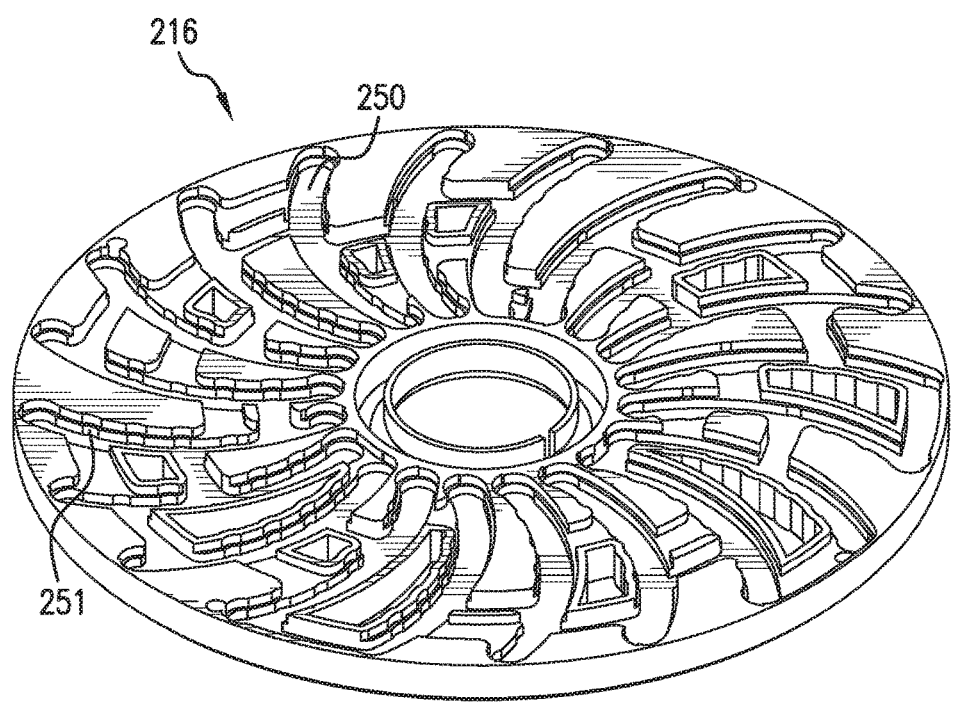
Figure 6C:
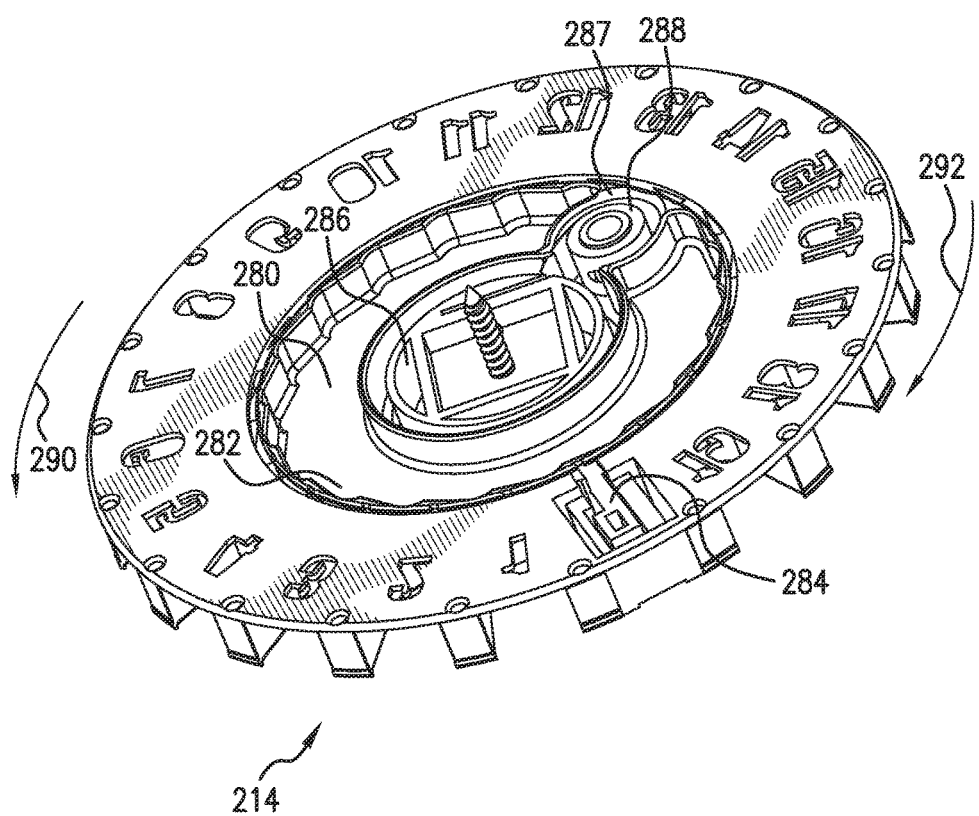

Another embodiment of the invention is shown in FIGS. 6A-6C. The container 200 comprises an outer shell or housing 212 with an upper portion 212a and a lower sealing portion 212b which is used to seal the internal components and medication inside once it is fully assembled. Inside the housing is drum 214 and combination disk 216. Pegs 220 are mounted on a peg carrier plate or cover 270 that, holds the pegs in position against the top portion 212a. The pegs move within respective arcuate channels 272. Top portions 222 of the pegs 220 extend through openings in the upper portion 212a of the housing. Rotary dials 262 can be attached to the top portions 222 of the pegs 220. The dials 262 can include a pointer or indicator that points to indicia 264. Rotating the dials allows a user to move the pegs into each of the predefined positions within the channels 250 in the disk 216. Because the pegs move along an arcuate path, the rest channels 250 in the combination disk 216 are also arcuate as shown in FIG. 6B.

With reference to FIG. 6C, this embodiment 200 includes a spring-loaded ratchet disk 280 having a plurality of ratchet teeth 282 formed along its circumference and which engage an elastic ratchet pin 284. The drum 214 and disk 216 can rotate about the ratchet disk 280. The drum 214 and disk 216 can be mechanically rotational locked to each other by various means. A central pillar (not shown) which extends from the bottom of the upper housing portion 212 acts as a rotation center for the combination disk 216, but a permanently fixed point for a Ratchet Disk Sleeve 286. A constant force coil spring 288 is coiled in region 287 inside the ratchet disk. One end of the spring 288 is attached to the ratchet disk 286. Turing in a winding direction 290 winds the torsion spring around the sleeve, which creates a constant torsion force tending to spin the drum in the other direction 292. The angles of the ratchet pin 284 and teeth on the drum allows the ratchet disk to spin in the winding direct 290 during a winding process, but not the other direction due to the drum being coupled to the immobile combination disk (which cannot move unless the pegs are in the correct position). A screw can be used to attach the sleeve to the central pillar, which locks the Ratchet Disk from falling out of the device but preserves its ability to rotate.

As noted, winding the spring primes the device for operation. When the correct peg position combination is entered, the spring will cause the disk 216 and drum 214 to automatically advance to the next dispensing position due to the force applied by the ratchet disk 216. With reference to FIG. 6B, the rest channels 250 can be configured with groove detents 251 in the direction of intended rotation that match the potential transition channel locations for different size pegs. These grooves act as catch-detests, which help the pegs snap into position and aid setting of a proper peg combination due to the constant force applied by the ratchet disk on the combination disk. As in prior embodiments, an outer ratchet system (not shown) can be used to prevent the disk spinning backwards in the transition channels.

A sticker or an engraving can be placed on a flat face of the top outer-shell 212a to provide a serial number, phone number, instructions for operation, and other information and indicia.

The top 212a of the housing has an opening 238 on its perimeter. This opening is positioned to align with a possible drum dispensing locations. Medication can be accessed or dispensed through opening 238 after the drum makes a rotation to a dispensing position. Alternatively, the opening 238 can be formed on the bottom 212a of the housing.

For loading by a pharmacist, the empty device 200 comes without the bottom 212a attached. The pharmacist simply loads the proper dosage into each chamber or puts a blister packed drum pre-loaded with the medicine in place. The bottom 212a can then be put in place and pressed down until it locks. If preloaded by manufacturer, the drum can be blister packed or equivalently sealed according to preset dosages for specific drugs. The packed drum is then simply dropped on top of the ratchet disk assembly, which would attach with the disk through one or more coupling points. A sticker with the prescription or other relevant information can be placed on the bottom cover 212a.

Preferably, the sealing cover 212b is amber or opaque and provides proper ultra-violet protection for the medication. It can be designed to shatter or break irreversibly if removed forcibly after the container is sealed.

Figure 7:
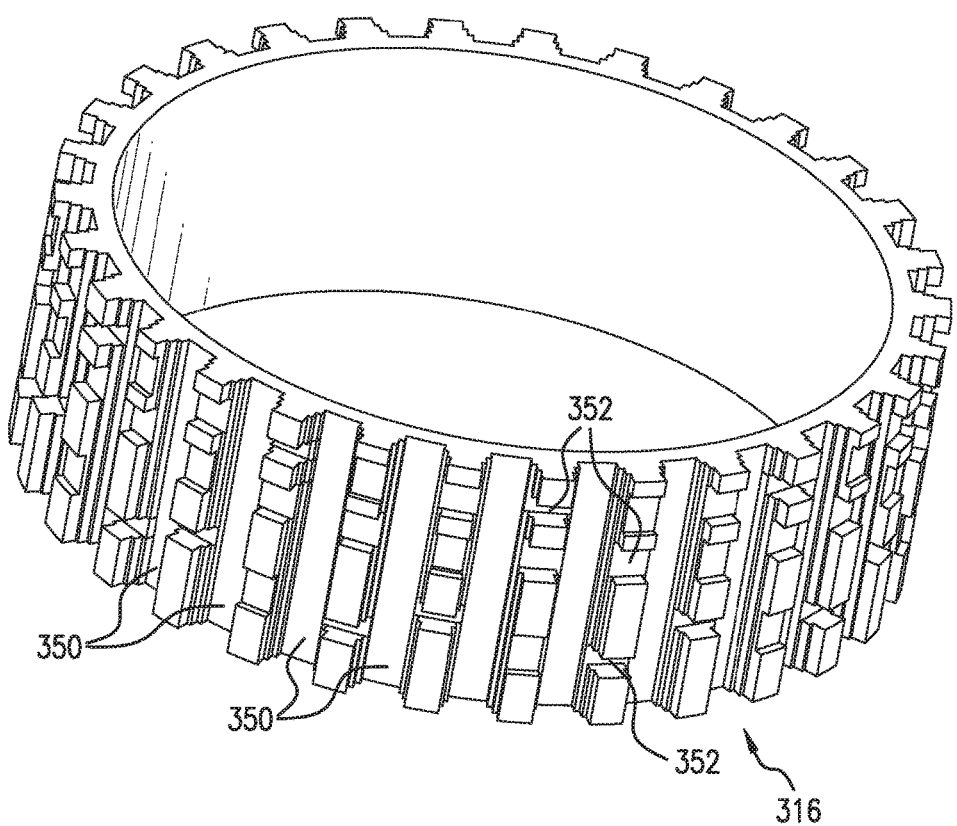
FIG. 7 is a perspective view of an embodiment of a combination cylinder.

The embodiments addressed above have been described with respect to a combination disk with the rest and transition channels formed on a surface thereon. In an alternative arrangement, the channels can be formed positioned around the periphery of the drum, as opposed to its top surface. FIG. 7 shows a combination cylinder 316 which can be rotationally coupled to a cylindrical pill drum (not shown). The combination cylinder 316 has a plurality of vertical rest channels 350 and circumferential transition channels 352. In this configuration, movable pegs are positioned on the side of the housing instead of its top and various mechanisms be used as will be appreciated by one of ordinary skill in the art to position the pegs relative to the housing and combination cylinder and to allow the pegs to be moved. The geometry of the rest and transition channel cross-section and of the pegs which engage the channels can be the same as addressed above.

As will be appreciated, each container requires a series of combinations to advance the pill drum through each of the dispensing positions. Various methodologies can be used to track the combinations for each particular container that is dispensed and to the combinations to a patient at appropriate times.

A back-end digital infrastructure comprises a database for managing the passwords and other data and can have multiple ways of access. For example, the database can be accessed to request a combination through a mobile phone/tablet application, a laptop application, a web (browser) based application, a text based system or a call-in based system. The database will process a patient's password requests for each new dose and either provide or deny such password based on a doctor's prescription instructions entered into our database by the pharmacist or the doctor directly. Upon receipt of the password, the patient can use it to access the relevant dose or chamber in the dispensing device. Medication access timing can preferably be amended in real time by the patient's doctor or other suitable person with suitable legal and/or other authority to access the specific patient's prescription in the database.

The back-end digital servers, apart from just processing password requests can be used for monitoring each patient's drug intake progress related to his/her diagnosis, while collecting relative medical data. By using the physical profile (e.g. weight, height, age . . . ), the interface supplies warning and educational messages. These messages can range from drug side effects to warnings of abnormal usage behavior warnings to other custom feedback. Abnormal usage behavior warnings are generated from deviations in historically collected data and dose timings from other patients with similar diagnosis and profile. The physical profile and diagnosis can be provided by the patient, pharmacist or preferably the doctor.

The server, network and data infrastructure that interact with the patient's front-end software can have various embodiments. The user's front-end software interacts with the server through different methods to request the passwords and other data transfers. Such methods include mobile or web applications, text-in service, call-in service or email (Collectively, the "Interface").

Figure 8A:
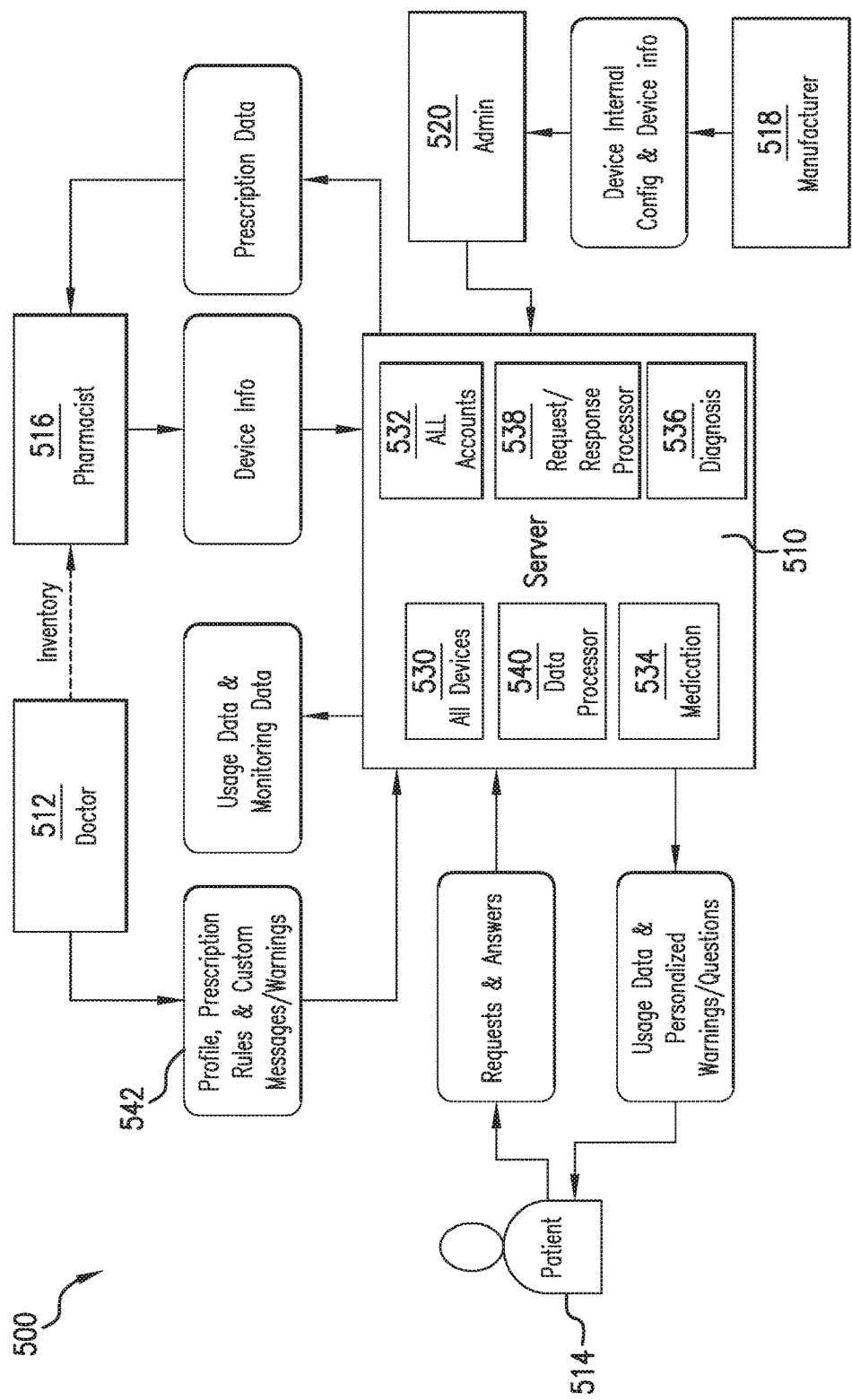
FIG. 8A is a high level illustration of a server providing functions to support the dispensing, monitoring, use, and use of a container according to aspects of the invention.

FIG. 8A is a high level illustration of a server 510. The server facilitates permissible data transfer amongst different parties which include, but are not limited to doctors 512, patients 514, pharmacist 516, manufacturers of the devices 518, various administrators 520 and others, such as medical insurers and government agencies. Below is a list of the simplified operations of different modules and data transfers of the server.

Devices Module 530 contains the list of all devices, which may be split into "unused", "in-use" or "archived" sections. The unused device section holds the first form of the device "data object", which is created by using data sent by the manufacturer comprising information about the physical internal mechanics of the device along with its device ID and other related data. An algorithm can be used with this data to create the password list and assign it to the digital object, along with other parameters like date created, maximum pill quantity, device model and more. Unused device can be located by the doctor or pharmacist portals for assignment of prescription rules, profiles and specific patient accounts.

After assignment, the object is transferred into the "in-use" section. The patient's front-end software can now interact with the object through server commands. Once the device is returned or is not returned after a designated amount of time, this data object is moved into an archived section. This includes the list of devices that have been used in the past and their data collected.

The device object can be sectioned into three parts. First, the device data issued by the admin system includes specific device pill passwords, the device ID and access code, type of device, and other related data. Second, the prescription data which is either created by the doctor or pharmacist from doctor's script. The prescription data is the rule set that the server follows to provide or deny pill passwords. The third, is the profile which is provided by the doctor or in some cases self-reported by the patient. The profile holds the diagnosis and the physical characteristics of the patient.

Accounts Module 532 stores and manages user accounts related to the system. These types of accounts include patients, doctors, pharmacists and other parties interested in interacting with the system. This section also optionally holds patient accounts which can be anonymous. This is possible because the device data object and not the patients name can be treated as the account since the device can be accessed through a device id and access code which are printed on the device. The device ID will never change, but the access code can be temporary and the patient can change it at will. The device data object can be assigned individual patient names either by loading from an existing patient account list, which holds all personal information, or directly during the data process.

Medication Module 534 portion of the server stores and processes medication related data. This list can be transferred to the doctor or pharmacist from the request processor when assigning prescription data. This information can also transferred to the patient for providing educational information about the medication they are taking. The doctor and pharmacist preferably would only select from an existing list of drugs to create a stable and uniform data sorting and entry. However custom drugs can be assigned during prescription entry by the doctor and added to the list later.

Figure 8B:
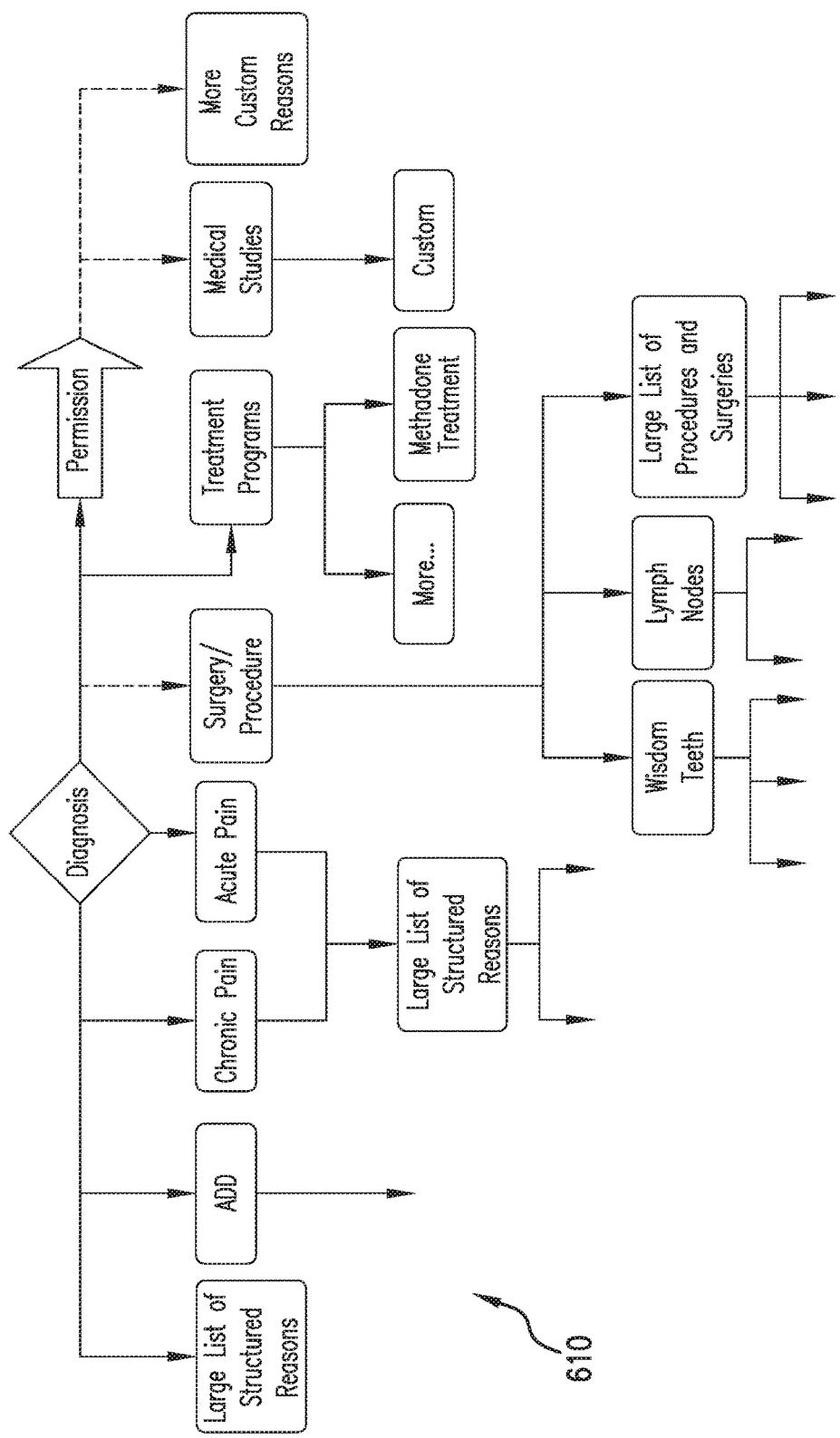
FIG. 8B is a sample of a diagnosis and action tree.

Diagnosis Module 536 stores and processes all the diagnoses issued by the doctor or self-reported by the patient. The diagnosis is what the doctor deems is the reason for taking the medication. A pre-set list(s) of diagnoses 610 can be presented to the doctor (see FIG. 8B) which creates uniform data entry, for sorting and querying diagnoses. The diagnosis can be used by the data processor to create trends, graphs and mean/max usage data for specific medications for specific a diagnosis.

Figure 8C:
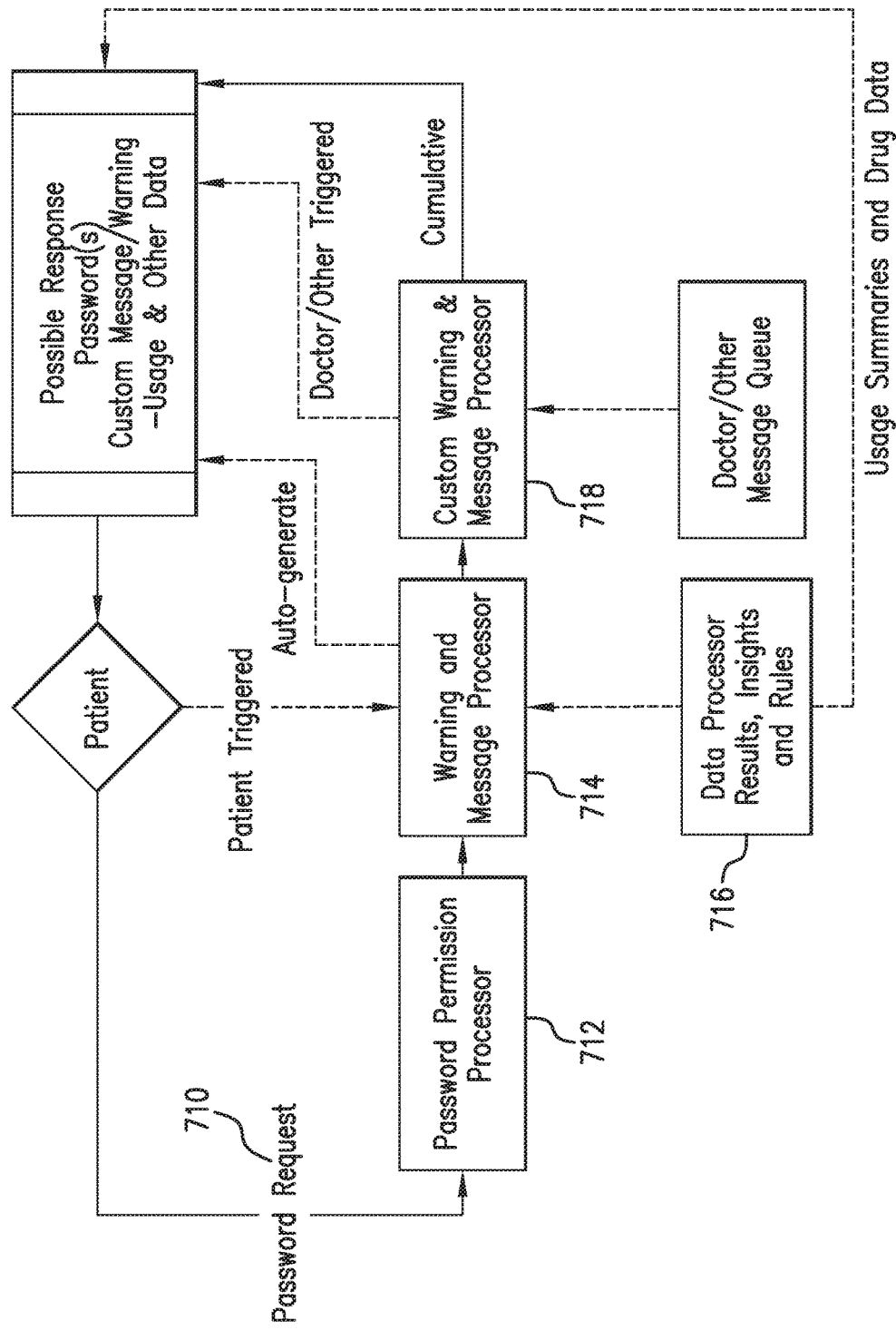
FIG. 8C is a simplified flow diagram of a password request and monitoring process.

Request/Response Processor Module 538 handles all the requests and responses from different parties. The patient can trigger a response by requesting a password (FIG. 8C, ref. 710) which goes to the Password Permission Processor 712 which looks at a rule set in the prescription data and rules set attached to the device account. The response can contain either a password or a deny message. The password request can also trigger a check in the Warning and Message Processor & Custom Warning Message Processor 714 to recalculate any auto-message that should be sent to the patient. The Warning and Message Processor 714 looks at the summaries from the Data Processor Results 716 which can store historic data to the profile and prescription held by the device object. The Custom Warning & Message Processor 718 looks at queued messages or rules set by the doctor directly through their portal. The patient front-end software and server can trigger or request responses and requests directly from both Message Processors. Relevant requests can be logged into the device object or other areas of the server which include dates and time stamps of password requests, the response results, pain level reports and their time stamps, other relevant answers to any messages, and more.

Figure 8D:
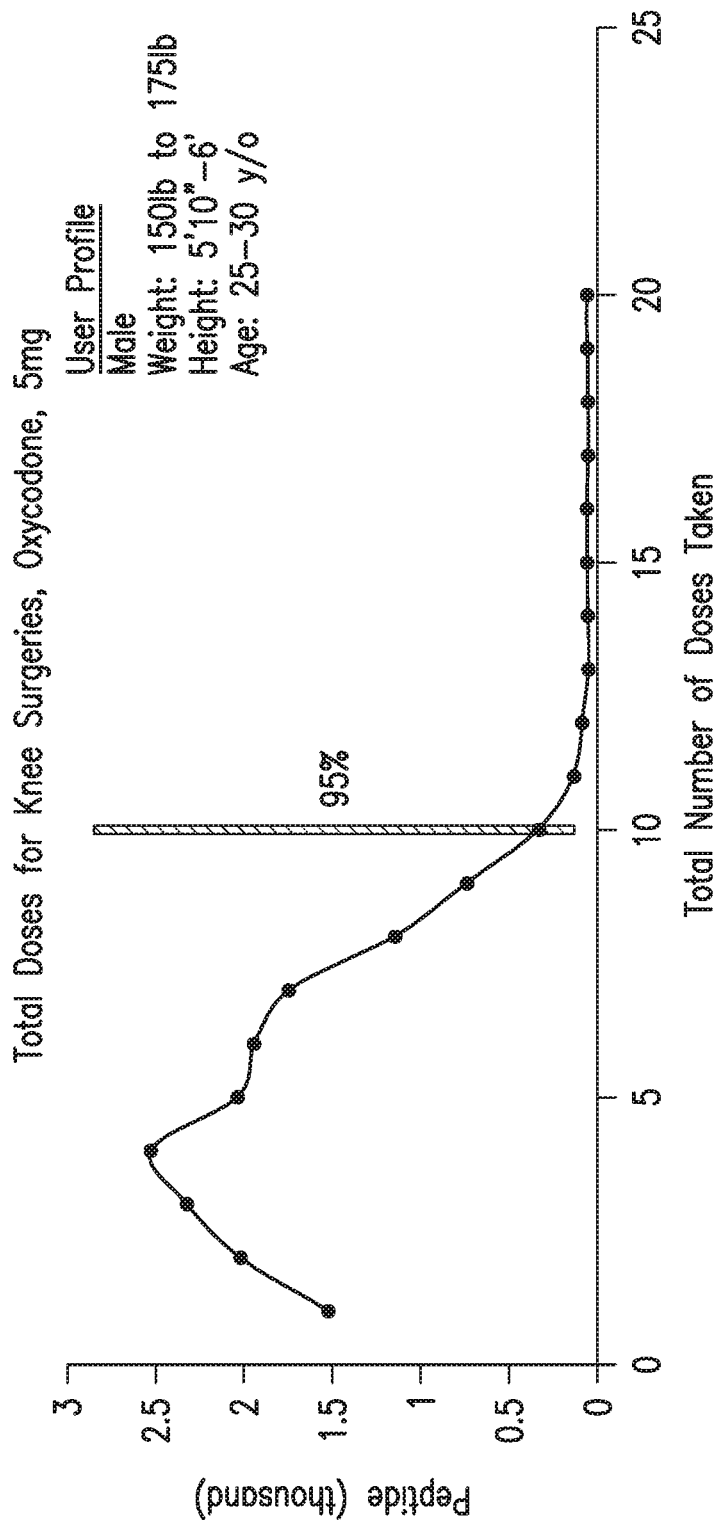
FIG. 8D is a sample trend analysis graph.

Data Processor Module 540 performs post-processing of all usage data by active or archived devices. The data processor can use mathematical interpolation and trend building techniques to summarize usage for drug and profile parameters. As an example, FIG. 8D shows a trend assemble by the processor on a specific surgery for the listed drug with a specific patient profile. It also shows the message trigger, either automatic or set by the doctor. The trigger will send a warning to the patient with the presented profile and drug criteria when they reach the 95% mark. This mark represents when 95% of patients have stopped taking their medication. The percentages and triggers for automatic messaging is set by regulated by medical research, doctor's request or patient's agreement to such values. The doctor can also be alerted when such triggers or criteria are reached. The data processor is also responsible to send similar trend data to the patient and/or doctor directly. The patient can use this data to self-monitor while having access to useful statistical usage data related to their condition. The doctor can use this statistical data during the profile and prescription assignment phase to more accurately choose the quantity and dose timing which would be based on actual population usage data.

In practice, the doctor 512 fills out the patient's profile while providing the prescription rules 542 for a specific drug that he wishes to prescribe. The doctor may use the data provided by the Data Processor Module as guidance for proper dosage and rules set. The doctor then sends the profile and prescription rules to a participating pharmacy, while indicating where to pick up the device. The doctor may also use the provided device return data on patients who have previously used the system. This can help doctors avoid giving dangerous medication to patients who have not returned devices or tampered with them which is a potential sign of improper use.

The pharmacist 516 loads the profile and prescription information the doctor has sent and loads the device, either by using a prepacked pill drum or by manually loading a drum. The pharmacist then assigns the device ID to the patient profile and gives the patient the device with the loaded medication. The pharmacist can include a pre-paid mailer with the device so a patient can return the empty device for recycling.

The patient 514, once in possession of the device and mailer, starts a pill password request cycle. The patient can use any method to request a pill password, including mobile/web application request, text-in, call-in or email. The patient can in some cases to fill out their physical profile and diagnosis. The patient can be provided with certain questions and warnings either auto-created by the front-end application or auto-generated by the server, which include pain-levels and other medically relevant data for collection purposes. The patient can receive the historic drug and diagnosis summaries from the server, which allows the patient to self-monitor by comparing their usage patterns with the national or regional averages. The patient is preferably required to return the device when prompted by the server or the medication runs out.

The device is returned in a pre-paid mailer. Devices that are not returned or show signs of tamper are logged in a database and this information can be made available to participating doctors, patients, and other parties. If the device is not empty when it is returned, the returned pills are counted and logged. The excess medication is destroyed. The can then recycled or prepped for re-use.

The device server objects are generated by the information sent by the manufacturer which include the device internals which include disk/dial types, any offsets and device identification numbers. An algorithm is used by the server with this information to generate the password list for the device object and then stored as "unused". This allows doctors and pharmacists to assign it to a patient profile during the loading process.

Various aspects of the invention have been disclosed and described herein. However, various modifications, additions and alterations may be made by one skilled in the art without departing from the spirit and scope of the invention as defined in the appended claims. Particular features of one embodiment can be implemented in other embodiments and one embodiment can use mechanical components described in connection with a different embodiment. For example, the embodiments can be manufactured as handle driven or wind-up configurations, with arcuate or radial and non-linear channels, with or without ratchet systems, and using a locking combination cylinder instead of a combination disk. Other combinations and permutations are also possible.

What is claimed is:

1. A container for restricting access to controlled objects comprising:
   a housing with a central axis, a top, and a bottom, and having an access port therein;
   an object storage drum within the housing, the drum being rotatable about the axis relative to the housing and having a plurality of dispensing positions including a start dispensing position and an end dispensing position, each dispensing position allowing access to a respective dispensing portion of the drum through the access port;
   a combination element rotatable about the axis relative to the housing, the combination element being rotationally lockable to the drum and having a surface with a plurality of channels formed therein;
   a plurality of pegs engaging the channels in the surface, each respective peg being movable between a respective plurality of predefined peg positions, the housing having indicia thereon indicating the respective pluralities of predefined peg positions;
   when the combination element is rotationally locked to the drum the plurality of channels defining for each respective peg a traversal path through which the respective peg can travel as the drum is rotated from the start dispensing position to the end dispensing position, the traversal path for each respective peg requiring the respective peg to be in a first predefined peg position to permit rotation of the drum between a respective first pair of adjacent dispensing positions and a second predefined peg position to permit rotation of the drum between a respective second pair of adjacent dispensing positions, wherein rotation of the drum requires the plurality of pegs to follow the respective traversal paths;

the particular positions of the plurality of pegs required to permit rotation of the drum from a current dispensing position to a next dispensing position defining a transition peg combination for the current dispensing position.

2. The device of claim 1, wherein the combination element is a disk on a top of the drum, the surface having the channels formed therein being a top surface of the disk.

3. The device of claim 2, further comprising an axial shaft, the axial shaft having a first engaging surface configured to engage a mating surface on the drum so as to rotationally lock the drum to the shaft when so engaged, the axial shaft having a second engaging surface configured to engage a mating surface on the disk so as to rotationally lock the disk to the shaft when so engaged.

4. The device of claim 3, wherein the mating surface on the disk is an interior surface of an axial hole in the disk and the mating surface on the drum is an interior surface of an axial hole in the drum.

5. The device of claim 3, wherein the axial shaft is movable along the axis and has a first position in which the first engaging surface engages the mating surface of the drum and the second engaging surface is not engaged with the mating surface of the disk, wherein, when the shaft is in the first position, the drum can be freely rotated relative to the disk and when the shaft is in the second position, the drum is rotationally locked with the disk.

6. The device of claim 2, further comprising a spring connected to a shaft about which the drum can rotate, the spring applying a torque to urge rotation of the drum about the axis; wherein when the drum is in the current dispensing position and the pegs are positioned in the transition peg combination for the current dispensing position, the applied torque urges the drum to rotate to the next dispensing position.

7. The device of claim 1, wherein the combination element is a cylinder surrounding the drum, the surface having the channels formed therein being an outer surface of the cylinder.

8. The device of claim 1, wherein the plurality of channels comprise
a plurality of rest channels, each peg engaging a respective rest channel when the drum is in a dispensing position and movable within the respective rest channel to each of the plurality of predefined dispensing positions; and
at least one transition channel connecting each pair of adjacent rest channels, each transition channel being in alignment with a respective one of the plurality of predefined peg positions.

9. The device of claim 8, wherein each peg is linearly movable along a radius extending from the axis and the rest channels are radially linear.

10. The device of claim 8, wherein each peg depends from a respective rotatable element, the rest channels following an arcuate path.

11. The device of claim 8, wherein each peg has a respective shape selected from a plurality of predefined peg shapes;
the rest channels each having a universal cross section through which any of the predefined peg shapes can pass; and
each transition channel having a respective cross section through which at least one of the predefined peg shapes can pass and which blocks passage of at least one other of the predefined peg shapes.

12. The device of claim 1, the drum having a plurality of chambers formed therein, each chamber being associated with a respective dispensing position and having an opening therein coincident with the access port when the drum is rotated to that respective dispensing position.

13. The device of claim 1 further comprising a ratchet pawl engaging teeth on one of the combination element and the housing so as to allow rotation of said one of the combination element and the housing in only one direction.

14. The device of claim 1, each respective peg having a top portion extending out of the housing through respective openings in the housing, at least some of the pegs are offset relative to the respective top portion of the peg, the respective peg configured for placement in the housing in one of two different orientations.

15. A container for restricting access to controlled objects comprising:
a generally cylindrical housing with a central axis, a top, and a bottom, and having an access port therein;
a generally cylindrical object storage drum within the housing, the drum being rotatable about the axis relative to the housing and having a plurality of dispensing positions including a start dispensing position and an end dispensing position, each dispensing position allowing access to a respective dispensing portion of the drum through the access port;
a plurality of pegs within the housing, each peg being movable between a respective plurality of predefined peg positions, the housing having indicia thereon indicating the respective pluralities of predefined peg positions;
each dispensing position having an associated peg position combination, adjacent dispensing positions having different peg position combinations,
means for preventing rotation of the drum from a current dispensing position to a next dispensing position unless the plurality of pegs are positioned in the peg position combination associated with the current dispensing position.

16. The container of claim 15, wherein the drum comprises blister packed pills, each pill in the blister pack being associated with a respective dispensing position and being accessible through the access port when the drum is at the associated dispensing position.

17. The container of claim 15, wherein the drum comprises a plurality of chambers, each chamber having an opening therein and being associated with a respective dispensing position, the opening for a particular chamber being accessible through the access port when the drum is at the dispensing position associated with that chamber.

18. The container of claim 15, further comprising a handle for rotating the drum from the current dispensing to the next dispensing position.

19. The container of claim 15, further comprising a coiled spring applying a rotational torque to the drum, the applied torque urging rotation of the drum from the current dispensing to the next dispensing position.

20. The container of claim 15, wherein the means for preventing rotation of the drum comprises:
- a disk in the housing between the drum and the pegs;
- the disk having a plurality of rest channels therein, each peg engaging a respective rest channel at each respective dispensing position and movable within the respective rest channel to each of the respective plurality of predefined peg positions;
- the disk having a plurality of transition channels, at least one transition channel connecting each pair of adjacent rest channels, each transition channel being in alignment with a respective one of the plurality of predefined peg positions; and
- each peg having a shape selected from a plurality of predefined peg shapes, wherein the rest channels are shaped to allow each of the predefined peg shapes to slide therein, wherein each transition channel is shaped to permit at least one predefined peg shape to slide therein and to block passage of at least one other of the predefined peg shapes.

* * * * *